United States Patent
Bennarsten et al.

(10) Patent No.: US 7,000,610 B2
(45) Date of Patent: Feb. 21, 2006

(54) HIGH FREQUENCY OSCILLATOR VENTILATOR

(75) Inventors: Johan Bennarsten, Gustavsberg (SE); Goran Rydgren, Bunkeflostrand (SE); Christer Strom, Pieta (SE)

(73) Assignee: Maquet Critcal Care AB, (SE)

( * ) Notice: Subject to any disclaimer, the term of this patent is extended or adjusted under 35 U.S.C. 154(b) by 91 days.

(21) Appl. No.: 09/733,064

(22) Filed: Dec. 11, 2000

(65) Prior Publication Data
US 2001/0003984 A1 Jun. 21, 2001

(30) Foreign Application Priority Data
Dec. 17, 1999 (SE) .................................. 9904645

(51) Int. Cl.
*A61M 16/00* (2006.01)
*A62B 7/00* (2006.01)

(52) U.S. Cl. ..................... 128/204.18; 128/204.21; 128/205.18

(58) Field of Classification Search ........... 128/203.12, 128/203.24, 203.25, 204.23, 204.26, 205.14, 128/207.14, 207.18, 204.18, 204.21, 205.15, 128/207.16, 205.19, 205.16, 205.18
See application file for complete search history.

(56) References Cited

U.S. PATENT DOCUMENTS

| | | | |
|---|---|---|---|
| 4,637,386 A | | 1/1987 | Baum |
| 4,665,911 A | * | 5/1987 | Williams et al. ........ 128/204.21 |
| 4,747,402 A | | 5/1988 | Reese et al. |
| 4,747,403 A | * | 5/1988 | Gluck et al. ........... 128/204.21 |
| 4,788,974 A | | 12/1988 | Phuc |
| 4,805,612 A | * | 2/1989 | Jensen ................... 128/204.21 |
| 4,821,709 A | | 4/1989 | Jensen |
| 4,838,259 A | * | 6/1989 | Gluck et al. ........... 128/204.21 |
| 5,092,326 A | | 3/1992 | Winn et al. |
| 5,165,398 A | * | 11/1992 | Bird ...................... 128/204.25 |
| 5,419,768 A | * | 5/1995 | Kayser .................. 128/205.19 |
| 5,555,880 A | | 9/1996 | Winter et al. |
| 5,862,802 A | | 1/1999 | Bird |
| 6,435,182 B1 | * | 8/2002 | Lutchen et al. ........ 128/200.24 |

FOREIGN PATENT DOCUMENTS

| | | |
|---|---|---|
| EP | 1 106 197 | 6/2001 |
| GB | 2 177 311 | 1/1987 |

* cited by examiner

*Primary Examiner*—Glenn K. Dawson
*Assistant Examiner*—Michael Mendoza
(74) *Attorney, Agent, or Firm*—Schiff Hardin LLP

(57) ABSTRACT

A high-frequency oscillator ventilator has a first gas conduit with an opening for gas connection with a patient's airways and a bias gas flow inlet and a bias flow outlet disposed to define therebetween a flow path for a bias gas within the first conduit. An oscillator operable to alternately introduce a volume of additional gas from a source into, and to withdraw at least the same volume of gas from, the first gas conduit, thereby inducing pressure oscillations in gas within the first conduit to move gas along a path intersecting the flow path for a bias gas alternately into and out of the opening at a predetermined high-frequency dependent on the output of a control signal generator.

2 Claims, 3 Drawing Sheets

HIGH FREQUENCY OSCILLATOR VENTILATOR

BACKGROUND OF THE INVENTION

1. Field of the Invention

The present invention relates to a high frequency oscillator (HFO) ventilator.

2. Description of the Prior Art

High-frequency (HF) ventilators may be classified as belonging to one of two categories, namely the high-frequency jet (HFJ) ventilator and the HFO ventilator.

The HFJ ventilator operates to fully ventilate a patient by supplying jet pulses of breathing gas to a patient's airways. These jet pulses are typically supplied through a narrow cannula at a frequency of between 2.5 Hz and 10 Hz, at a pressure of between 0.2 bar and 2.7 bar and with a tidal volume of around 2 to 5 milliliters (ml) per kilogram (kg) body weight of a patient. This high pressure jet pulse causes the lungs to expand during an inspiration phase in which the desired tidal volume is supplied. The expiration phase is essentially passive and results from the natural compliance of the lungs which tends to collapse them and expel the gas. In a modification to this basic HFJ ventilator it is known to provide a Venturi vacuum device in communication with the patient's airways on the expiration side of the ventilator. This device creates a vacuum of typically between 0.002 and 0.025 bar during expiration to promote the natural collapse of the lungs. However expiration is still effectively passive, relying on the compliance of the lungs to push out the supplied gas.

The HFO ventilator operates to fully ventilate a patient by introducing pressure oscillations to a column of gas in communication with a patient's airways. These oscillations cause the supply of breathing gas to and the active extraction of at least the supplied volume of gas from the airways of the patient, in alternation. It is this active extraction of the supplied volume that is the primary difference between HFO and HFJ ventilation systems. The peak-to-peak pressure amplitude about an average airway pressure is typically between 0.05 and 0.2 bar and oscillates at a typical frequency of between 10 Hz and 50 Hz to supply a tidal volume significantly less than required during spontaneous breathing, typically at or around anatomical dead-space volumes, and is usually less than that typically supplied by the jet device during HFJ ventilation.

Both types of HF ventilators operate in marked contrast to a conventional mechanical ventilator. The conventional ventilator operates to fully ventilate a patient by supplying breathing gas to the patient's airways in an amount and at a frequency substantially equal to those of a spontaneously breathing patient. Typically then, for an adult, the conventional mechanical ventilator will provide a tidal volume of around 500 milliliters at a frequency of around 0.2 Hz.

The HFO ventilator generally has a gas conduit with an opening at one end for connection to the patient's airways and an opposite end in gaseous communication with an oscillator. The oscillator includes a reciprocally moveable element, such as a membrane or a piston, as part of a variable gas holding volume to which the end of the conduit is in gaseous communication. A drive unit is provided to reciprocate the moveable element at a predetermined high-frequency to alternately remove a volume of gas from and return it to the gas conduit. Over-pressure and under-pressure pulses are thereby supplied to gas within the conduit at that frequency. This causes a column of gas, the volume of which is dependent on the volume change of the oscillator, to be moved along the gas conduit into and out of the patient's airway and thereby to provide ventilation. A continuous so-called "bias" flow of fresh breathing gas moves along a flow path between an inlet and an outlet and intersects the path of the moving column within the conduit to flush through the outlet carbon dioxide-rich gas that has passed from the patient's lungs. This bias flow also maintains an average positive airway pressure (or bias) about which pressure the high-frequency pressure pulses oscillate. A disadvantage of the known HFO ventilator is that a large percentage (typically over 70%) of the volume of gas moved by the variation in oscillator volume never reaches the patient and is lost from the conduit through the outlet. The volume change of the oscillator therefore must be made commensurately larger in order to supply an adequate tidal volume to the patient. As a result it becomes increasingly difficult to maintain the necessary volume changes as the oscillation frequency increases and tidal volumes may then become insufficient. An additional problem is that the gas conduit itself must be made of a relatively stiff material so that the energy of the pressure pulses generated by the oscillator is not reduced through work done in expanding and contracting the conduit. Such a length of stiff conduit makes the HFO ventilator cumbersome to deploy.

SUMMARY OF THE INVENTION

This object is achieved in accordance with the invention in a high-frequency oscillator ventilator wherein the oscillator includes an arrangement for alternately introducing a volume of additional gas into a gas conduit in connection with a patient's airways, and withdrawing this volume of additional gas from the conduit, to produce pressure oscillations.

By generating oscillations by alternately introducing and withdrawing a volume of additional gas sufficient to provide a desired tidal volume to the patient's airways, the disadvantage of reciprocating the large moveable element of the known HFO ventilator is removed.

Preferably, the oscillator is adapted to introduce the additional gas proximal the opening in the first gas conduit which is intended for connection with the patient's airways. This reduces dead-space, allows a more flexible tubing to be used for the remainder of the conduit away from the opening without the risk of energy being lost in expanding and contracting the tubing, and permits smaller volumes of gas to be used in order to generate the desired pressure oscillations.

Conveniently, the additional gas may be introduced by a pulse generator via a second conduit which opens into the first and its removal may be accomplished by a separate device via the first, the second or even a third conduit. The increased design flexibility provided by providing separate means for introducing and for removing gas also allows each of the means to be optimised for its intended purpose.

DESCRIPTION OF THE PREFERRED EMBODIMENTS

Figure 1:
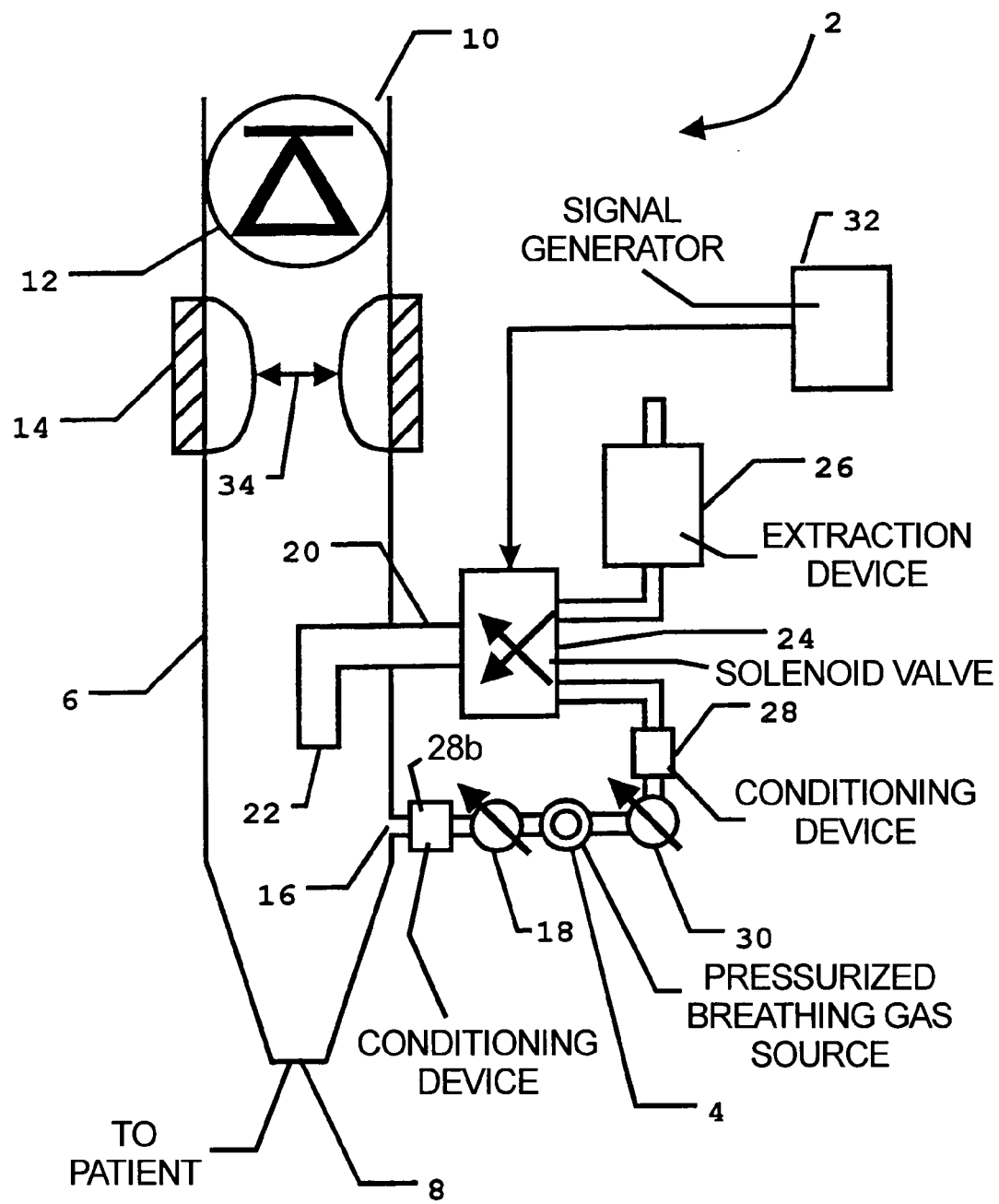
FIG. 1 shows a first embodiment of an HFO ventilator according to the present invention.

In FIG. 1, an HFO ventilator 2 is shown in operative connection to a source of pressurized breathing gas 4. The HFO ventilator 2 is configured to utilize the source of breathing gas 4 both as a bias flow and as a source of an additional gas, as will be described below. The source of breathing gas 4 may conveniently be a conventional mechanical ventilator adapted to provide a continuous flow output.

The HFO ventilator 2 is provided with a primary conduit 6 that has a patient opening 8 at one end which is intended to be placed in gas communication with a patient's airways, for example by connection to a conventional endotracheal tube (not shown). A vent opening 10 is also provided in the primary conduit 6 through which gas may be vented to atmosphere (as shown) or to a known gas recovery means (not shown). A one-way valve 12 is disposed within the primary conduit 6, proximal the vent opening 10 and is configured to prevent gas entering the conduit 6 through the vent opening 10. A variable aperture throttle valve 14 is also disposed in the primary conduit 6 at a location proximal the one-way valve 12. A bias gas flow inlet 16 is connectable to the source of pressurized breathing gas 4 via a pressure regulator 18 and is connected to the primary conduit 6 at a location proximal the patient opening 8. A secondary conduit 20 terminates with an opening 22 in the primary conduit 6 proximal to and directed toward the patient opening 8. A solenoid valve 24 switchably connects the secondary conduit 20 either to an extraction device 26, such as a rotary or reciprocating vacuum pump, or to a conditioning device 28. The extraction device 26 is vented to atmosphere (or alternatively to a gas recovery means which may be formed in part by a conventional mechanical ventilator, if used, where gas analysis can be done and perhaps used to monitor the efficacy of the HFO treatment) and the conditioning device 28 is connected to the source of pressurized breathing gas 4 via a pressure regulator 30. A control signal generator 32 is operably connected to the solenoid valve 24 to provide it with control signal pulses which cause the valve 24 to alternately connect the conditioning device 28 and the extraction device 26 to the secondary conduit 20 at a predetermined and preferably variable frequency which is typically between 10 and 50 Hz. As a safety feature, the solenoid valve 24 may be designed to remain in a "neutral" state in the absence of a control signal from the signal generator 32 in which state neither of the devices 26,28 are connected to the secondary conduit 20. The supply of an alternating positive and a negative signal from the control signal generator 32, such as a sine or square wave signal, then causes the solenoid valve 24 to connect respectively the conditioning device 28 or the extraction device 26 to the secondary conduit 20 in an alternating manner dependent on the polarity of the supplied signal.

During the use of the HFO ventilator 2 a continuous bias gas flow is provided by gas from the source 4 preferably via a conditioning device 28b, through the primary conduit 6 between the inlet 16 and the vent opening 10. This establishes an average airway pressure within a patient's airways which maintains the patient's lungs in a partially inflated condition throughout ventilation. The average airway pressure may be regulated by adjusting one or both of the pressure regulator 18 and the aperture 34 of the throttle valve 14. Gas from the source 4 also passes through a different pressure regulator 30 to a conditioning device 28 where moisture may added and/or the moist gas warmed. The solenoid valve 24 is operated in response to electrical pulses from the control signal generator 32 to periodically connect the moist gas from the conditioning device 28 to the secondary conduit 20 in order to generate gas pulses at a predetermined frequency and for a predetermined time. In this manner pulses of additional fresh gas are introduced into the primary conduit through the opening 22 in the secondary conduit 20. Because of relative dispositions of the opening 22, the patient opening 8 and the bias gas inlet 16 then each pulse need only consist of a volume of gas substantially equal to the tidal volume necessary to provide adequate ventilation at the operating frequency of the HFO ventilator. As with the known HFO ventilator this desired tidal volume can be calculated as being between one and four ml per kg body weight of the patient. This additional gas induces a pressure increase in the gas within the primary conduit 6 similar to that associated with the known HFO ventilator. This causes a similar volume of gas to be moved through the patient opening 8 and to the patient's lungs where gas exchange occurs to transfer oxygen ($O_2$) into the lungs and carbon dioxide ($CO_2$) into the gas. After the delivery of each pulse the signal from the signal generator 32 causes the solenoid valve 24 to connect the extraction device 26 to the conduit 20 for a predetermined time so as to withdraw through the opening 22 at least the same volume of gas which was pushed out of the patient opening 8 by the immediately preceding pulse of additional gas. This induces a pressure decrease in the gas within the primary conduit and causes a similar volume of gas to be moved out of the patient's lungs. Gas entering the primary conduit through the patient opening 8 is relatively rich in $CO_2$ and is flushed from the system through the one-way valve 12 by the bias gas flowing from the inlet 16 to the vent opening 10.

It will be appreciated by those skilled in the art that the conditioning device 28 may be omitted or may be replaced with a conventional heat and moisture exchanger connected to receive both the withdrawn gas and the additional gas pulse to transfer heat and/or moisture from the former to the latter without departing from the invention as claimed.

Figure 2:
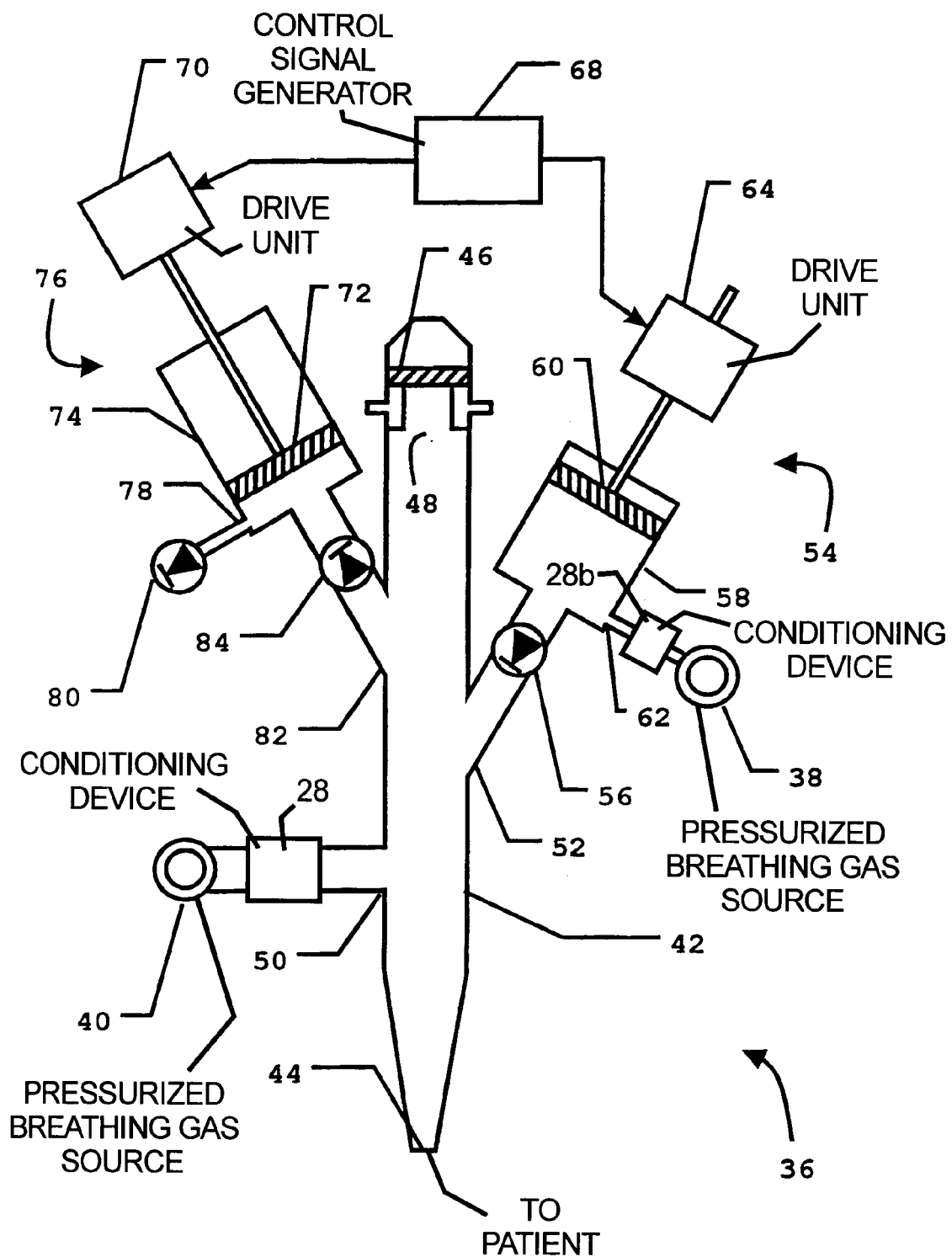
FIG. 2 shows a second embodiment of an HFO ventilator according to the present invention.

In FIG. 2, an HFO ventilator 36 is shown in operative connection to a first source of pressurized breathing gas 38 which in use will act as an additional gas source and to a second source of pressurized breathing gas 40 which in use will act as a bias gas supply. The HFO ventilator 36 has a primary conduit 42 that has a patient opening 44 at one end which is intended to be placed in gaseous communication with a patient's airways, for example by connection to a conventional endotracheal tube (not shown). A mushroom valve 46 terminates a vent opening 48 in the primary conduit 42. A bias gas flow inlet 50 is connectable to the bias gas flow supply 40 through a conditioning device 28 so that a continuous flow of bias gas can be introduced into the primary conduit 42 proximal the patient opening 44, and which exits via the vent opening 48 when the pressure within the conduit 42 exceeds the closing bias of the mushroom valve 46. This pressure is then the average airway pressure established by the HFO ventilator 36 in use. A side branch 52 of the primary conduit 42 connects to a gas pulse generator 54 through a one-way valve 56 which is arranged so that gas can only flow from the gas pulse generator 52. The gas pulse generator 54 comprises a first variable gas holding volume 58 having a reciprocally moveable element, here a piston 60 as one wall and an inlet 62 connected to the source of additional gas 38 through a conditioning device 28b. A first drive unit 64 is include to reciprocate the piston 60 at a predetermined high-frequency dependent on a signal output from a control signal generator 68. The control signal generator 68 also supplies a control signal to a second drive unit 70 which is operably connected to a piston 72 of a second variable gas holding volume 74 of an extraction device 76. The second variable gas holding volume 74 is provided with a vent 78 which is here shown to connect to atmosphere via a one-way valve 80. A further side branch 82 connects the second variable volume 74 to the primary conduit 42 via a one-way valve 84. The two one-way valves 80,84 are mutually arranged so that gas can only flow from the side branch 82 and out of the vent 78 as the piston 72 is reciprocated.

The HFO ventilator 36 operates broadly as described with respect to the HFO ventilator 2 of FIG. 1. Thus, in use, a bias flow is provided between the inlet 50 and the vent opening 48 to pressurize gas within the primary conduit 42 and a patient's airways until an average airway pressure is established which is dependent on the opening pressure of the mushroom valve 46. A pulse of additional gas is supplied to the primary conduit 42 by the gas pulse generator 54 so as to intersect the flow path of the bias gas. The gas pulse is generated as the piston 60 is moved to reduce the volume of the variable gas holding volume 58 and thereby force gas out of the connecting side branch 52. As the piston 60 is moved to increase the volume of the variable gas holding volume 58, fresh gas is supplied to that volume 58 from the gas source 38. Alternately with the supply of the additional gas pulse by the generator 54, gas is withdrawn from the primary conduit 42 by the extraction device 76. The piston 72 is moved to increase the volume of the second variable gas holding volume 74 and thereby draw in gas from the conduit 42. As the piston 72 is moved in the opposite direction gas is forced from the variable volume 74 through the vent 78. As described above in connection with the ventilator 2 of FIG. 1, the alternating supply to and withdrawal from the primary conduit 42 of a volume of gas causes oscillations in the column of gas within the conduit 42 (and consequently within a patient's lungs) at a frequency dependent on the frequency of reciprocation of the pistons 60,72.

The control signal generator 68 can provide an independently variable signal to each of the piston drive units 64,70 so that at least the phase difference between each the control signals can be varied. In this way withdrawal of the gas by the extraction device 76 can begin slightly before the end of the delivery of the gas pulse by the generator 54 to provide a smooth transition between supply and withdrawal of gas. This also allows compensation for delays caused by differences, for example in length, of conduits connecting the gas pulse generator 54 and the extraction device 76 to the primary conduit 42.

Additionally the stroke lengths of the two pistons 60,72 may different and variable to allow more gas to be withdrawn than was supplied. The bias flow can be adjusted to compensate for this net loss of gas from the primary conduit 42 which promotes the removal of $CO_2$ from the ventilator 36.

Figure 3:
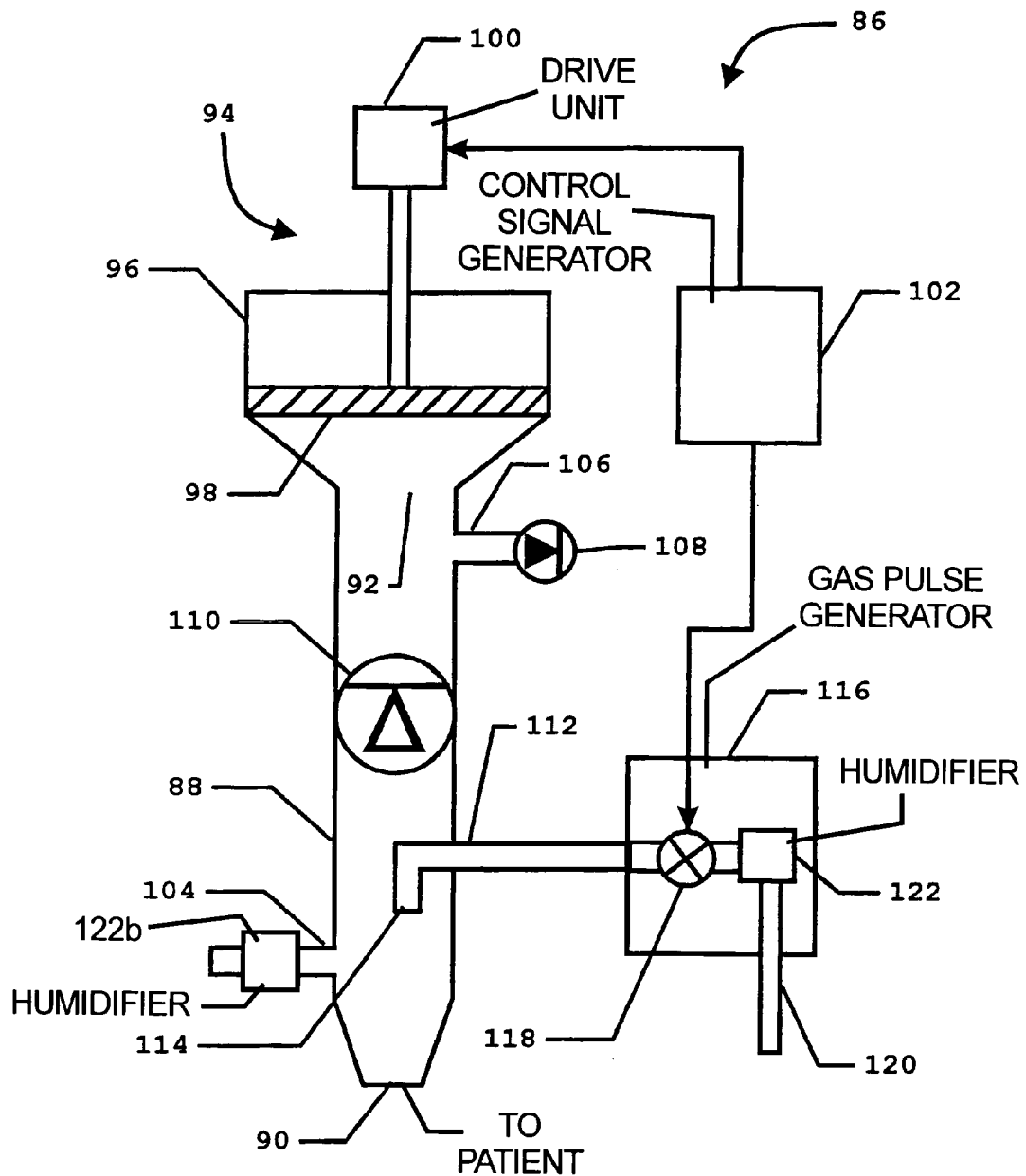
FIG. 3 shows a third embodiment of an HFO ventilator according to the present invention.

In FIG. 3 an HFO ventilator 86 is shown having a primary gas conduit 88 with a patient opening 90 at one end and with an opening 92 at the opposite end connected to an extraction device 94. The extraction device 94 has a variable gas holding volume 96 which has a reciprocally moveable element, again shown as a piston 98, as a defining wall section. The piston 98 connects to a drive unit 100 which reciprocates the piston 98 at an operating frequency of the HFO ventilator 86 dependent on an oscillating control signal provided by the control signal generator 102. A bias gas flow inlet 104 connects to the inside of the primary conduit 88 at a location proximal the patient opening 90 and a gas outlet 106 connects to the inside of the primary conduit 88 via a humidifier 122b at a location distal the patient opening 90 and in gas communication with the variable gas holding volume 96. The inlet 104 and outlet 106 are disposed to define a flow path therebetween for bias gas within the primary conduit 88. A one-way valve 108, for example a mushroom valve, is located at the gas outlet 106 and arranged to allow the only the venting of gas from the primary conduit 88. This valve 108 is adapted to open only when pressure within the primary conduit 88 reaches a predetermined and possibly adjustable level. In this way a desired average airway pressure can be established by the HFO ventilator 86. A further one-way valve 110 is located within the primary conduit 88 to prevent gas passing from the variable volume 96 and through the patient opening 90 as the piston 98 is moved to reduce the volume of the variable volume 96. A secondary conduit 112 is provided with an opening 114 in the primary conduit 88 through which gas may be directed to intersect the bias flow path and move towards the patient opening 90. A gas pulse generator 116 has a controllable on/off valve 118 which is switched under the control of the control signal generator 102 to alternately allow and prevent passage of gas from a pressurized source of an additional gas (not shown) which connects to an inlet 120 of the gas pulse generator 116. Also provided within the gas pulse generator 116, in-line between the inlet 120 and the valve 118, is a humidifier 122 which conditions the additional gas before it is supplied to the primary conduit 88.

In use the control signal generator 102 actuates the on/off valve 118 and the piston 98 in a timed relationship to alternately supply a pulse of gas to and withdraw gas from the primary conduit 88 and thereby oscillate gas therein at the desired operating frequency of the HFO ventilator and thereby effect ventilation of a patient.

It will be appreciated by those skilled in the art that non-inventive modifications may be made to the embodiments of FIGS. 1 to 3 or other embodiments devised while remaining within the scope of the invention as claimed. Thus, for example, although it is preferable to introduce the bias flow into the primary conduit 42 proximal the patient opening 44 this flow may be introduced distal the opening 44 and extracted proximal it. Additionally, the size variable gas holding volumes 58,74,96 may be of a known type other than a piston arrangement and may include a mechanically, pneumatically or electro-mechanically driven diaphragm or collapsible wall section.

Furthermore, some or all of the conditioning devices 28, 28b and the humidifiers 122, 122b may be omitted without departing from the invention as claimed.

We claim as our invention:

1. A high-frequency oscillator (HFO) ventilator comprising;
   a first gas conduit having an opening adapted for gas connection with a patient's airways and a bias gas flow inlet and a bias flow outlet disposed to define therebetween a flow path for a bias gas within the first conduit;
   an oscillator for inducing pressure oscillations in gas within the first conduit to move said gas along a path intersecting the flow path for a bias gas alternately into and out of the opening at a predetermined high-frequency, said oscillator comprising an arrangement for alternately introducing a volume of additional gas into said bias gas and withdrawing at least the volume of gas from the first gas conduit to induce the pressure oscillations.

2. An HFO ventilator as claimed in claim 1 wherein said arrangement in the oscillator is disposed to introduce the volume of additional gas into the first gas conduit to intersect the bias flow path at a location proximal the opening.

* * * * *